United States Patent [19]

Berger et al.

[11] Patent Number: 5,533,970
[45] Date of Patent: Jul. 9, 1996

[54] RETRACTABLE NEEDLE SYRINGE

[75] Inventors: Howard S. Berger, Hackensack; Robert B. Odell, Franklin Lakes; Sandor Gyure, West Orange, all of N.J.

[73] Assignee: Becton, Dickinson and Company, Franklin Lakes, N.J.

[21] Appl. No.: 314,030

[22] Filed: Sep. 28, 1994

[51] Int. Cl.$^6$ .................................................. A61M 5/00
[52] U.S. Cl. ........................................ 604/110; 604/195
[58] Field of Search .................................... 604/110, 228, 604/187, 218, 192, 243, 195, 198, 242

[56] References Cited

U.S. PATENT DOCUMENTS

| | | | |
|---|---|---|---|
| 4,747,830 | 5/1988 | Gloyer et al. | 604/110 |
| 4,790,822 | 12/1988 | Haining | 604/110 |
| 4,861,338 | 8/1989 | Mathiesen et al. | 604/110 |
| 4,919,652 | 4/1990 | Alter et al. | 604/110 |
| 4,935,015 | 6/1990 | Hall | 604/195 |
| 4,950,241 | 8/1990 | Ranford | 604/110 |
| 4,978,340 | 12/1990 | Terrill et al. | 604/195 |
| 5,047,016 | 9/1991 | Dolgin et al. | 604/110 |
| 5,112,315 | 5/1992 | Gloyer et al. | 604/195 |
| 5,188,597 | 2/1993 | Sweeney et al. | 604/110 |
| 5,188,601 | 2/1993 | King | 604/110 |
| 5,205,823 | 4/1993 | Zdeb | 604/110 |
| 5,205,824 | 4/1993 | Mazur | 604/110 |
| 5,242,400 | 9/1993 | Blake, III et al. | 604/110 |
| 5,256,151 | 10/1993 | Chul | 604/195 |
| 5,273,543 | 12/1993 | Bell | 604/110 |
| 5,304,154 | 4/1994 | Gloyer et al. | 604/240 |
| 5,308,329 | 5/1994 | Mazur et al. | 604/110 |
| 5,405,327 | 4/1995 | Chen | 604/110 |
| B1 4,507,117 | 5/1985 | Vining et al. | 604/196 |

Primary Examiner—Randall L. Green
Assistant Examiner—V. Alexander
Attorney, Agent, or Firm—John L. Voellmicke

[57] ABSTRACT

A retractable needle syringe includes a barrel having an inside surface defining a chamber, an open proximal end and a distal end. An elongate plunger is slidably positioned in fluid-tight engagement with the inside surface of the barrel. The plunger includes a distal end, a proximal end and a radially directed projection on its distal end. A movable carrier is positioned in fluid-tight engagement with the inside surface of the barrel. The carrier includes an outside surface, a distal end, a proximal end, and a passageway therethrough in fluid communication with the chamber. The proximal end of the carrier includes an open-ended groove which is sized and shaped to receive the plunger projection. The groove includes an axial portion and a circumferential portion. The plunger is movable axially so that the plunger projection can enter and exit the axial portion of the groove. Rotation of the plunger with respect to the carrier causes the projection to enter the circumferential portion of the groove, containing said projection so that said plunger rod can apply axially directed force and rotationally directed force to the carrier. A needle cannula projects outwardly from the distal end of the carrier. Control structure is provided to prevent movement of the carrier with respect to the barrel during normal use of the syringe and for allowing the carrier to be moved proximally into the chamber of the barrel through forces applied to the plunger.

21 Claims, 9 Drawing Sheets

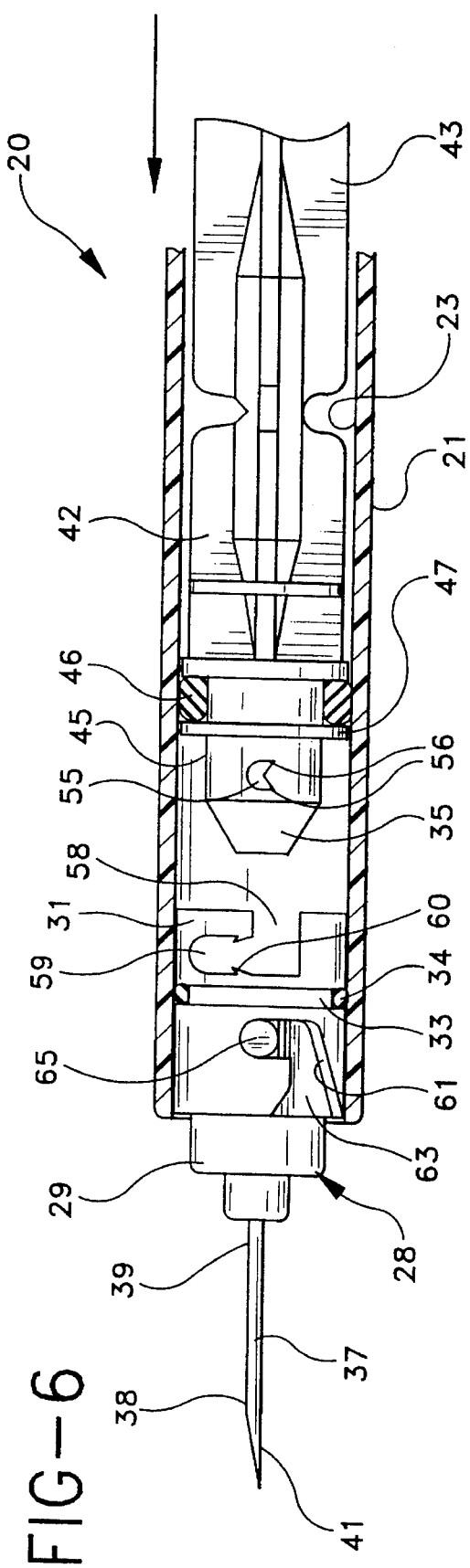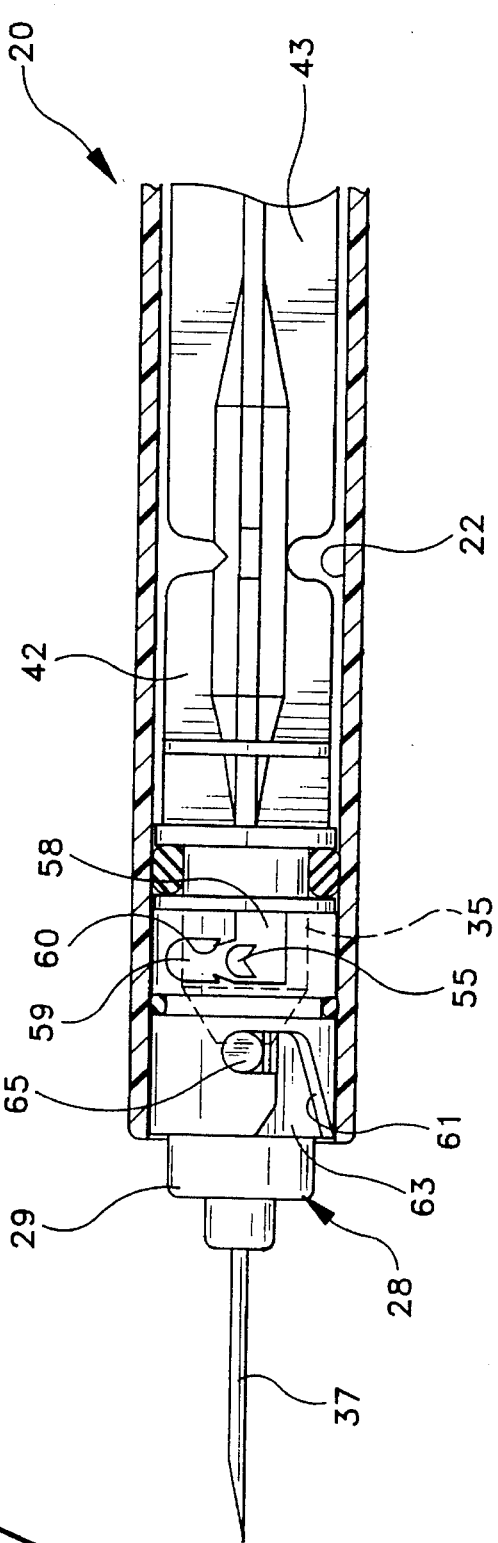

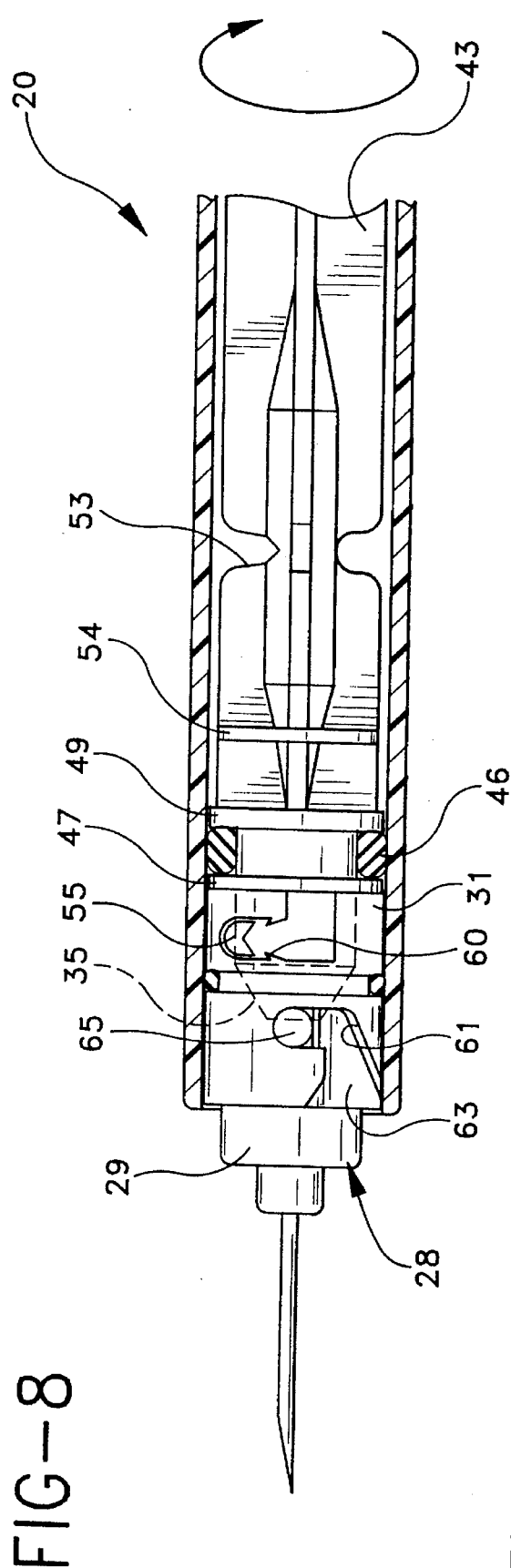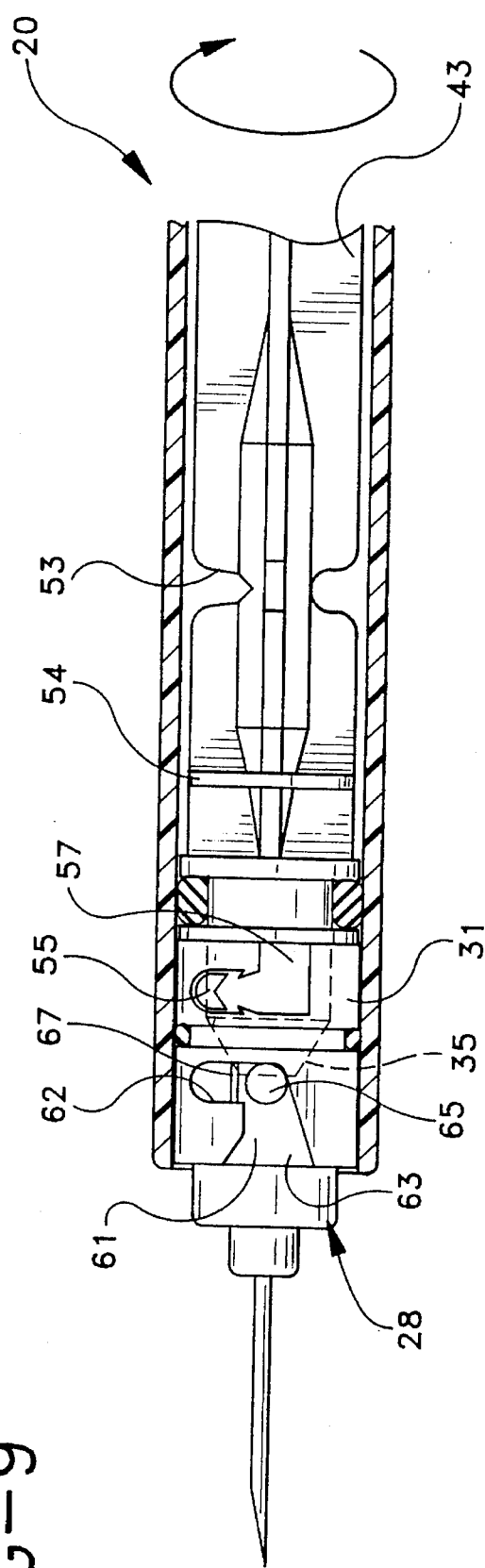
FIG-8
FIG-9

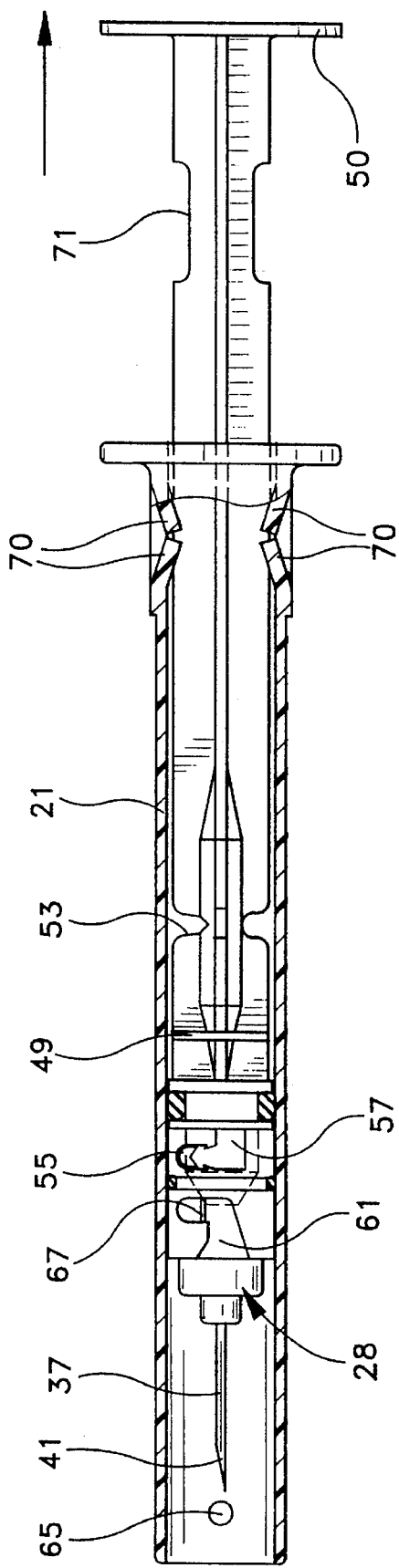
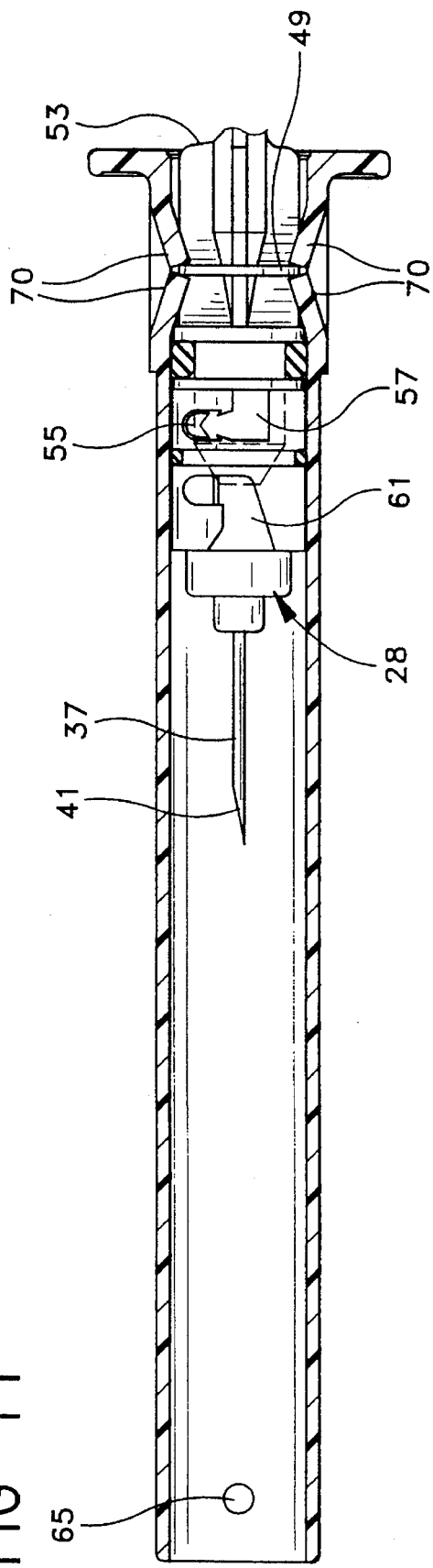

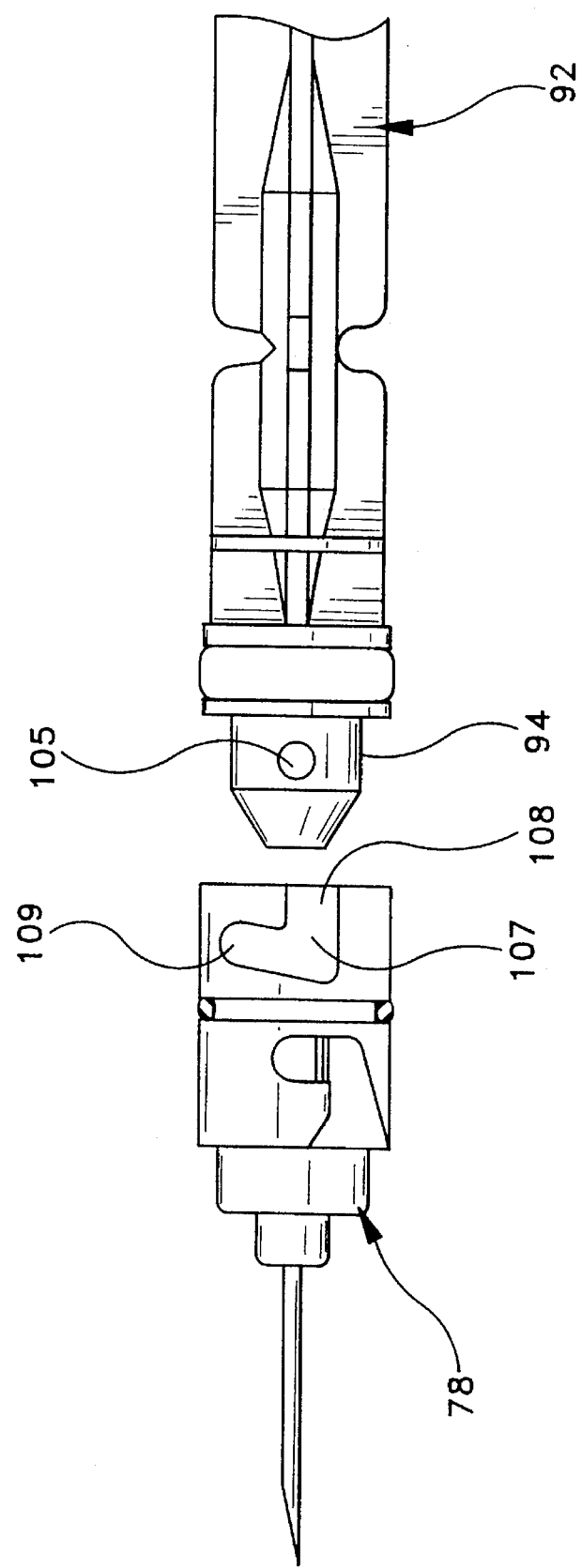

RETRACTABLE NEEDLE SYRINGE

BACKGROUND OF THE INVENTION

1. Field of the Invention

The present invention relates to hypodermic syringes. More particularly, the present invention relates to a syringe having structure for withdrawing the hypodermic needle into the syringe barrel after use.

2. Description of Related Information

Generally speaking, a syringe includes a cylindrical barrel commonly made of thermoplastic material or glass, having a distal end connected to a sharpened needle cannula and a proximal end adapted to receive a stopper and plunger assembly.

In recent years there has developed an increased concern regarding the transfer of disease, infection or the like to syringe users and health care professionals who accidentally, or through negligent handling, stick themselves with hypodermic needles while disposing of used hypodermic syringe products. In many areas in a hospital, where needle cannula products are used, disposal bins are provided so that a syringe or other needle cannula product may be immediately discarded in a safe rigid container. However, there are areas of medical practice, such as emergency rooms, where disposal containers are not readily available or practical, and where products having self-contained safety features are desirable. In theory, after such a syringe is used to inject medication or for another purpose, a safety device contained within the syringe is activated to prevent further contact with the sharp needle tip. One type of safety syringe includes structure which allows the withdrawal of the hypodermic needle into the syringe barrel to minimize the chance of further contact with the sharp needle tip. A syringe with its needle withdrawn can be more safely transported to a disposal system.

One such prior art retractable needle syringe includes a frangible zone which allows separation of the forward wall of the barrel, which is connected to the hypodermic needle, from the side wall of the barrel. The syringe also contains structure on the interior of the forward wall and the exterior of the piston for selectively attaching the piston to the forward wall so that the user can forcibly twist the piston to break the frangible means and draw the forward wall, including the hypodermic needle, into the syringe barrel. This design requires a compromise in the design of the syringe barrel. The barrel must be strong enough to remain intact during normal use yet weak enough to be sheared apart by any user regardless of strength.

Many prior art retractable needle syringes have deficiencies similar to that described above. In particular, the needle or the needle carrier of a retractable needle syringe must be securely held by the syringe barrel during normal use which often includes substantial hydraulic pressures experienced during injection especially with highly viscous liquids, and substantial forces including piercing rubber stoppers of medication vials. The syringe barrel must hold the needle carrier to a degree that it will not be overcome by the forces of normal use and still be disengagable through forces applied to a relatively flexible and weak plunger rod which extends from the open proximal end of the syringe barrel. Many prior art syringes recite designs that when made sufficient to withstand the forces of normal use, the needle or needle carrier cannot be easily disengaged. On the other hand, easy disengagement of the needle or needle carrier will lead to a structure that cannot withstand the forces of normal use.

Many prior art retractable needle syringes teach structures which require additional distal movement of the plunger to attach the plunger to the needle carrier or needle. Accordingly, after the injection process is completed, and the needle, is removed from the patient, the user advances the plunger rod further to secure the plunger rod to the needle carrier or needle for withdrawing into the syringe barrel. These structures leave valuable medication, or residual bodily fluid such as blood, in the syringe barrel. The volume of trapped or wasted medication is a function of the axial movement of the plunger from its position in the barrel at the end of injection to its further distal position in the barrel when it is secured to the needle or needle carrier. Also, this trapped medication or fluid is often forcibly expelled randomly into the healthcare environment while connecting the plunger to the needle carrier.

Many prior art syringe designs allow the repeated connection and disconnection of the plunger rod to the carrier and repeated withdrawal and re-exposure of the needle. Under certain circumstances this can be undesirable since it leads to accidental or unauthorized reuse of a contaminated syringe.

Also, most prior art retractable needle syringe designs do not provide structure for retaining the needle in its retracted position within the barrel, and although the needle may be permanently attached to the plunger rod preventing further reuse of the syringe, the needle may still be accidentally projected back out of the syringe where it presents a safety hazard.

Although the prior art teaches many different syringe assemblies having the capacity to withdraw the needle into the syringe barrel after use, there still exists a need for a simple, straight-forward, reliable, easily fabricated retractable needle syringe having locking structure for holding the needle in a position with respect to the barrel which is strong enough to resist the often substantial forces experienced during normal use and which is easily de-activated to lower the force required for withdrawing the needle into the barrel. There is also a need for a retractable needle syringe that does not waste medication by requiring additional axial motion of the plunger rod to secure the plunger rod to the needle carrier. There is also a need for a one-way locking mechanism so that when the plunger rod is secured to the carrier it will not disconnect from the carrier; finally, when the needle is withdrawn inside the barrel there is a need for the locking mechanism to prevent the needle from being later moved so that it projects out of the barrel.

SUMMARY OF THE INVENTION

A retractable needle syringe of the present invention includes an elongate barrel having an inside surface defining a chamber, an open proximal end and a distal end. An elongate plunger is slidably positioned in fluid-tight engagement with the inside surface of the barrel. The plunger includes a distal end, a proximal end extending outwardly from the open end of the barrel, and a radially directed projection on the distal end of the plunger rod. A movable carrier is positioned in fluid-tight engagement with the inside surface of the barrel, the carrier includes an outside surface, a distal end, a proximal end, and a passageway therethrough in fluid communication with the chamber. The proximal end of the carrier includes an open-ended groove which is sized and shaped to receive the plunger projection.

The groove includes an axial portion and a circumferential portion. The plunger is movable axially, distally and proximally, so that the plunger projection can enter and exit the axial portion of the groove. Rotation of the plunger with respect to the carrier causes the projection to enter the circumferential portion of the groove containing or trapping said projection so that said plunger rod can apply axially directed force and rotationally directed force to the carrier. A needle cannula projects outwardly from the distal end of the carrier. The cannula includes a distal end, a proximal end and a lumen therethrough in fluid communication with the passageway of the carrier. Control structure is provided to prevent movement of the carrier with respect to the barrel during normal use of the syringe while the control means is in a first locked position, and the allowing the carder to be moved proximally into the chamber of the barrel through forces applied to the plunger while the control means is in a second unlocked position. Transition between the first locked position and the second unlocked position and withdrawing the cannula into the barrel is accomplished by at least two motions of the plunger with respect to the barrel while the distal end of the plunger engages the carrier. The first motion is rotational to rotate the carrier with respect to the barrel through an acute angular rotation followed by a second axial motion proximally directed to move the carrier into the barrel far enough so that the distal end of the cannula does not extend beyond the distal end of the barrel.

BRIEF DESCRIPTION OF THE DRAWINGS

FIG. 6 is a partial cross-sectional side elevation view of the syringe of FIG. 1 illustrating the position of the plunger as medication is being expelled from the syringe.

FIG. 7 is the syringe of FIG. 6 illustrating the position of the plunger rod after medication has been expelled from the syringe.

FIG. 8 is the syringe of FIG. 7 illustrating the locking of the plunger to the carrier.

FIG. 9 is the syringe of FIG. 8 illustrating the unlocking of the carrier from the barrel.

FIG. 10 is the syringe of FIG. 9 illustrating the needle carrier and the needle withdrawn into the barrel.

FIG. 11 is the syringe of FIG. 10 wherein the needle carrier and needle are further withdrawn into the barrel to a locked position, and the proximal end of the plunger rod is broken off and removed from the distal end of the plunger rod.

FIG. 13 is an alternative embodiment of the carrier and plunger of the present invention.

DETAILED DESCRIPTION

Figure 1:
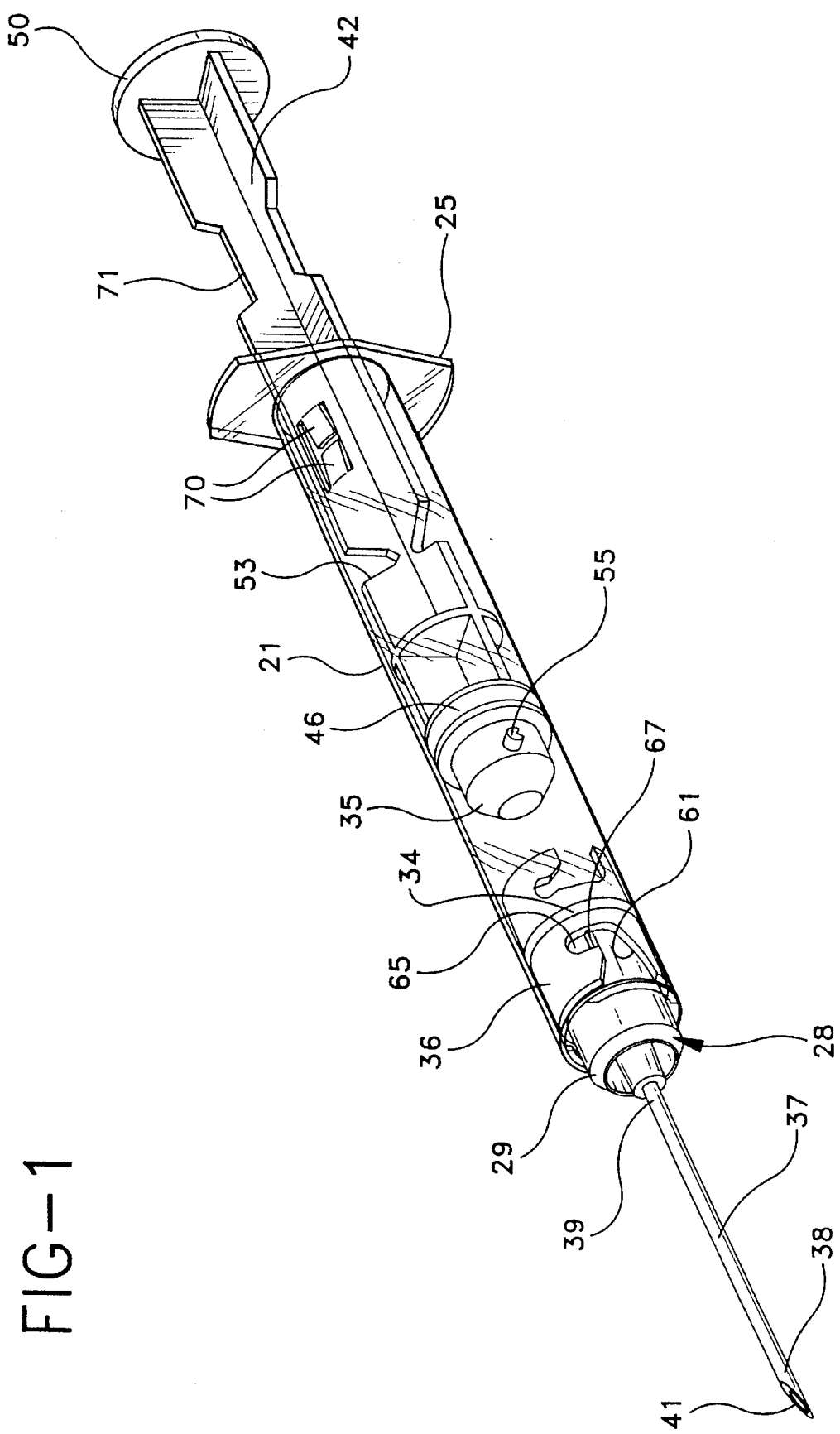
FIG. 1 is a perspective view of a preferred embodiment of the retractable needle syringe of the present invention.
Figure 2:
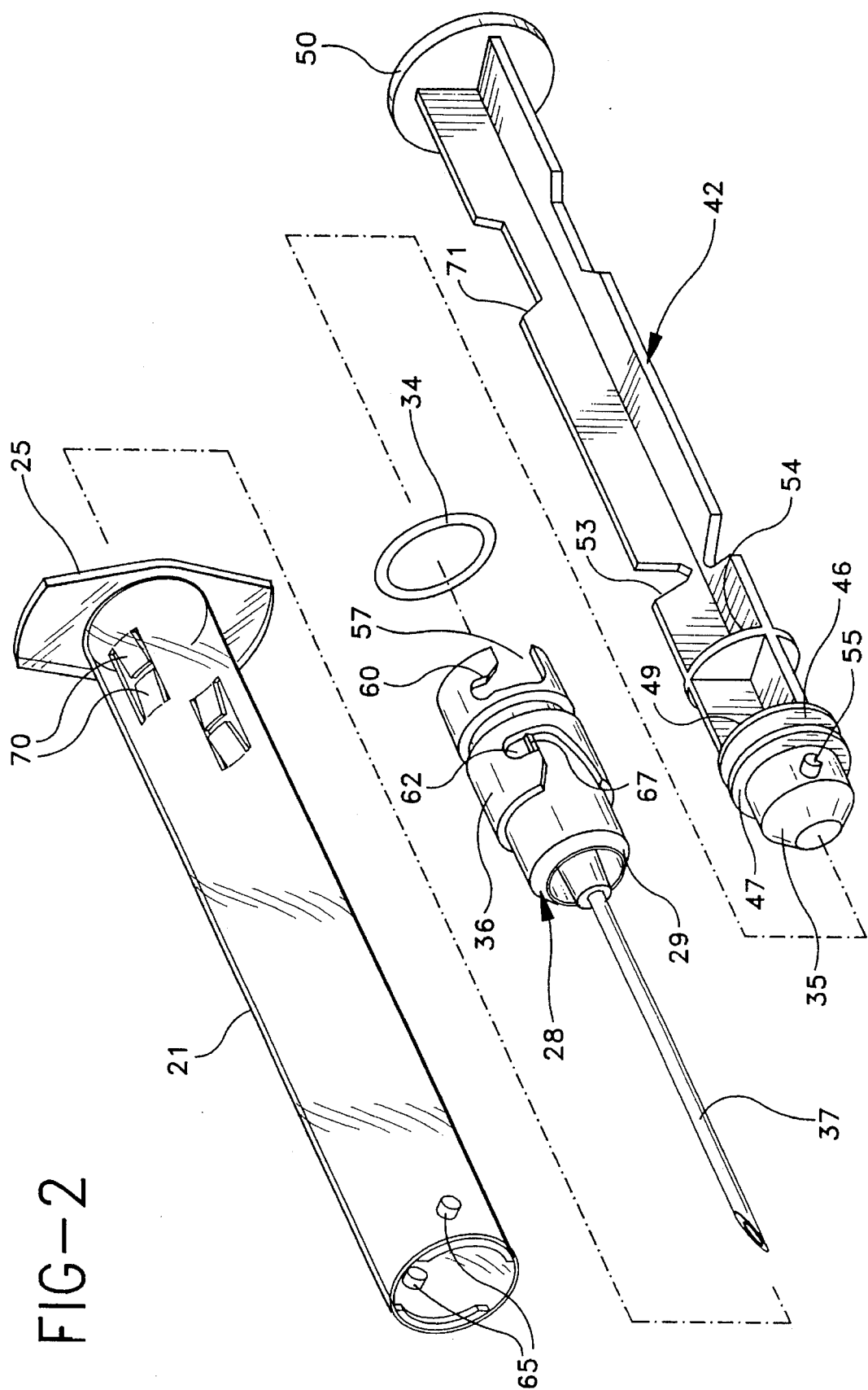
FIG. 2 is an exploded view showing the assembly of the syringe of FIG. 1.
Figure 3:
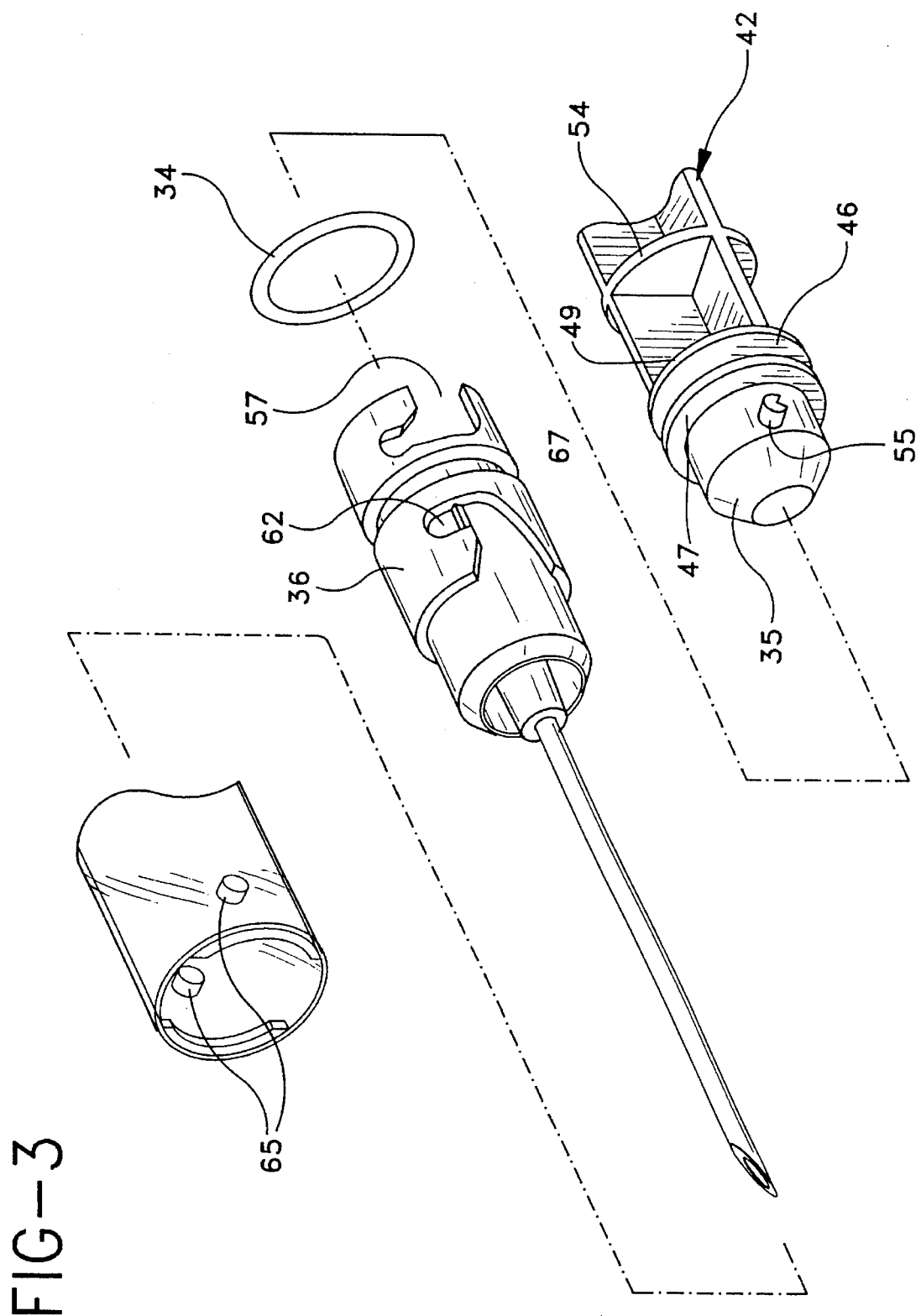
FIG. 3 is an enlarged partial view of FIG. 2 illustrating the distal end of the syringe barrel, the plunger rod and the carrier.
Figure 5:
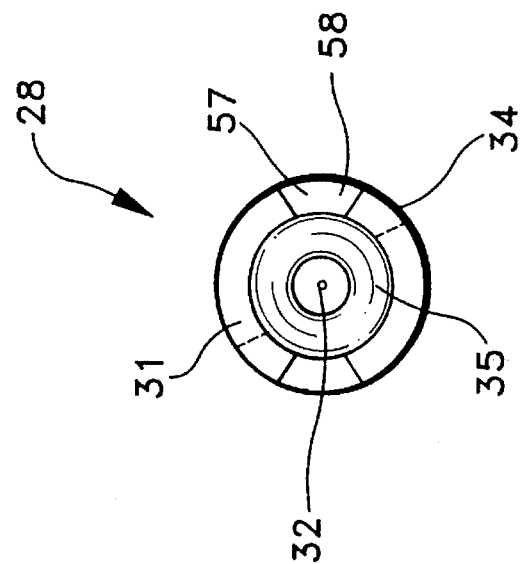
FIG. 5 is a side elevation view of the proximal end of the carrier of FIG. 3.
Figure 4:
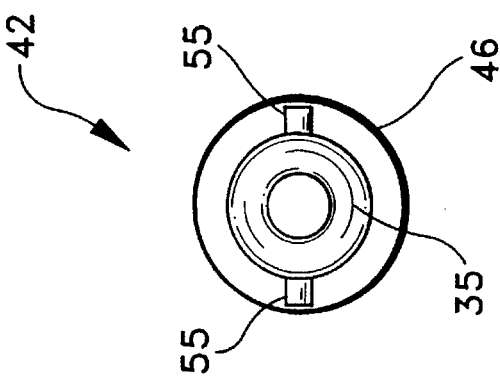
FIG. 4 is a side elevation view of the distal end of the plunger of FIG. 3.

While this invention is satisfied by embodiments in many different forms, there are shown in the drawings and will be herein described in detail preferred embodiments of the invention with the understanding that the present disclosure is to be considered exemplary of the principles of the invention and is not intended to limit the scope of the invention to the embodiments illustrated. The scope of the invention will be measured by the appended claims and their equivalents.

Adverting to FIGS. 1–11, a retractable needle syringe assembly 20 includes an elongate barrel 21 having an inside surface 22 defining a chamber 23. Barrel 21 also includes an open proximal end 25 and a distal end 27.

For the purposes of the description of the present invention, the term "distal end" is intended to refer to the end of the syringe from which the needle cannula projects, whereas the term "proximal end" is intended to refer to the end of the syringe closest to the holder of the syringe and furthest from the tip of the needle.

A movable needle carrier 28 is positioned in fluid-tight engagement with inside surface 22 of barrel 21 at distal end 27. The needle carrier includes a distal end 29, a proximal end 31 and a passageway 32 therethrough in fluid communication with chamber 23. In this preferred embodiment, the carrier includes circumferential groove 33. Annular elastomer ring 34 is positioned in groove 33 and contacts the inside surface of the barrel to help provide a fluid-tight engagement between the inside surface of the barrel and the carrier. The elastomeric ring can have a variety of cross-sectional shapes, such as circular, rectangular, square and the like. It is within the purview of the present invention to include a carrier without an elastomeric ring. Such a carrier can be made of plastic and have an annular rib molded in its body. The annular rib can be shaped to be resilient. Also, the annular rib could be rigid and a fluid-tight seal with the barrel can be achieved by relying on the resiliency of the barrel. Also, the carrier can be mounted to the barrel through threaded structure on the outside of the carrier and the inside of the distal end of the barrel.

A needle cannula 37 projects outwardly from distal end 29 of the carrier. Cannula 37 includes a distal end 38, a proximal end 39 and a lumen therethrough in fluid communication with passageway 32. The needle cannula in this embodiment includes sharpened distal tip 41 to facilitate use of the needle to pierce the skin for delivery of therapeutic liquids or the removal of bodily fluids such as blood. In this embodiment the needle is fixedly attached to the carrier.

The present invention includes a plunger 42 slidably positioned in fluid-tight engagement with the inside surface of the barrel. In this embodiment, plunger means includes an elongate plunger rod 43, having proximal end 44 and distal end 45, and an annular sealing ring 46 contained between distal sealing ring flange 47 and proximal sealing ring flange 49. Annular sealing ring 46 can have a variety of cross-sectional shapes, such as circular, rectangular, square and the like. The purpose of the sealing ring is to provide a fluid-tight engagement between the plunger and the barrel. It is within the scope of the present invention to include a plunger without a separate annular sealing ring. Such a plunger could be made entirely of plastic and have an annular rib molded around in the approximate position of the annular sealing ring 46 of the preferred embodiment. This rib, however, would be integrally molded with the plunger and shaped to be resilient or deflectable to achieve the fluid-tight seal with the barrel. Also, the annular rib could be formed to be relatively rigid and the barrel molded with a thin sidewall so that the fluid-tight seal is achieved through the deflection or resiliency of the barrel. The plunger rod is accessible outside of the proximal end of the barrel and is provided to move the sealing ring along the barrel to force fluid into and out of the chamber through the passageway. A plunger rod flange 50 is provided as a convenient structure for applying force to move the plunger rod with respect to the barrel. Barrel flange 51 is provided to assist the user in providing axial force between the plunger rod and the barrel.

Engagement means is provided for allowing the distal end of the plunger rod to engage the carrier for allowing proximally directed forces and rotational forces applied to the plunger to be transmitted to the carrier. In this embodiment, engagement means includes a radially directed projection 55 on distal end 45 of the plunger rod. In this preferred embodiment, there are two radially directed projections 55. The second radially directed projection is on the opposite side of the distal end of the plunger rod. Both projections will function in the same manner. Engagement means further includes an open-ended groove 57 on proximal end 31 of the needle carrier. Groove 57 is sized and shaped to receive plunger projection 55. Groove 57 includes an axial portion 58 and a circumferential portion 59. In this preferred embodiment, there are two open-ended grooves 57 with the second open-ended groove being on the opposite side of the carrier as the first open-ended groove. Proximal end 31 of the needle carrier includes recess 35 which is sized and shaped to receive the distal end of the plunger rod with minimal air space between the distal end of the plunger rod and the and the recess in the carrier. As best illustrated in FIGS. 6 and 7 the plunger is movable axially, distally and proximally, so that the plunger projection 55 can enter and exit axial portion 58 of groove 57. Rotation of the plunger with respect to the carrier causes projection 55 to enter circumferential portion 59 of the groove wherein the groove contains the projection so that the plunger rod can be used to apply axial directed and rotationally directed force to the carrier.

It is within the purview of the present invention to include a radial directed projection and a circumferential portion of the open-ended groove which are shaped to allow the projection to be positioned within the circumferential portion of the groove and removed from that portion, and subsequently reinserted and removed as many times as desirable. However, in the preferred embodiment, these elements are designed for a single use. Specifically, when the plunger is advanced to its most distal position, expelling medication in the syringe, the plunger rod may be rotated clockwise, as best illustrated in FIG. 8, to cause radial directed projection 55 to enter circumferential portion 59. In this preferred embodiment, the projection and the circumferential portion of the open-ended groove are configured so that when the projection is positioned in the circumferential portion, the projection is locked in the circumferential portion and cannot be removed therefrom. In this embodiment, the locking function is accomplished by having locking edges 56 on the projection which snap into and engage locking edges 60 of the circumferential portion, as best illustrated in FIG. 8. This feature prevents use of the syringe once projection 55 is locked into circumferential portion 59. Various shapes and configurations can be used for a projection which locks into the circumferential portion of the groove. Additional sheet metal fasteners may be used on the projection and/or in the groove to make a secure locking arrangement. Locking may also be accomplished through the use of encapsulated adhesive wherein the adhesive capsules are broken when the projection enters the circumferential portion of the groove. Also, it is within the purview of the present invention to have the projection extending radially inwardly from the recess in the carrier and have the groove formed on the distal end of the plunger. This embodiment would function in the same manner as described above with the projection moving from the plunger to the carrier and the groove moving from the carrier to the plunger.

The present invention includes control means for helping prevent movement of the needle carrier with respect to the barrel when the control means is in a first locked position, and for allowing the carrier to be moved proximally into said chamber when the control means is in a second unlocked position. The preferred embodiment, control means includes control groove 61 on outside surface 36 of the carrier. In this embodiment there are two control grooves, one on each side of the carrier. Each control groove includes a closed proximal end 62 and an open distal end 63. Inwardly directed projections 65 on the inside surface of the barrel are positioned within the grooves when the carrier is at the distal end of the barrel. In this embodiment, the projections are cylindrical having a circularly-shaped cross-section. As illustrated in FIGS. 6, 7 and 8, the projections prevent proximal and distal motion of the carrier with respect to the barrel when the projections are in closed ends 62 of control grooves 61. Accordingly, substantial axial force can be applied in a proximal or distal direction without forcing the carrier into the barrel or removing it from the barrel and rendering the syringe unusable. The distal end of the barrel may also have an inwardly projecting flange to resist distal motion of the carrier out of the barrel.

In order to help resist rotational motion of the carrier away from closed end 62 of the grooves with respect to projections 65, each groove includes a restriction or area of reduced depth 67 adjacent to closed end 62. The area of restriction or reduce depth is shallower than the length of projection 65 so that additional rotational force is required to move the carrier into and out of a position where projections 65 are positioned at closed ends 62 of the grooves. The restriction in this invention can also be an area of reduced width in the groove adjacent to the closed end which is configured so that additional rotational force is required to move the carrier into and out of the position where projections 65 are positioned at closed ends 62 of the grooves.

The syringe of the present invention can be used in the same manner as a conventional hypodermic syringe following known and accepted safe usage procedures. At the end of the injection stroke which delivers medication to the patient, as illustrated in FIG. 7, the user rotates the plunger clockwise with respect to the barrel, as illustrated in FIG. 8, so that the radial directed projection 55 on the distal end of the plunger rod enters circumferential portion 59 of open ended groove 57. In this preferred embodiment, the projection is now locked in the groove. Any attempt to unlock the projection will cause locking edges 56 on the projection to engage locking edges 60 in the open-ended groove. Accordingly, in a preferred embodiment, this step cannot be reversed.

It should be noted that a major advantage of the present invention is that it can be configured to expel almost all of the medication in the chamber during the injection process because additional distal movement of the plunger rod is not necessary to secure the plunger rod to the needle carrier, only rotational force is required to accomplish this result.

This preferred embodiment also includes means for aligning the plunger with respect to the barrel so that radial directed projection 55 on the plunger enters axial portion 58 of open ended groove 57 upon distally directed axial motion of the plunger only, without requiring the operator to rotate the plunger with respect to the barrel or the carrier. In the preferred embodiment, a substantial portion of the elongate plunger rod is formed of four longitudinal equally spaced ribs having a plus-sign shaped cross-section. The space between two adjacent ribs functions as a longitudinal groove along the plunger rod. Rotation of the plunger rod with respect to the barrel can be prevented by providing an inwardly directed tab or projection in the barrel which projects into the groove or the space between the ribs. In this embodiment an inwardly directed tab is formed by molding said barrel with H-shaped gap in the barrel wall resulting in cantilever tabs 70 being formed in the barrel wall. After molding, the cantilever tabs 70 are pressed inwardly through the use of pressure or pressure and heat to form inwardly projecting tabs as best illustrated in FIG. 10. These tabs prevent rotation of the plunger rod and can be used to align the plunger rod projection with the axial portion of the open-ended groove. Any inwardly directed projection, formed in the barrel or by a separate element attached to the barrel can be used to prevent retention of the plunger. After the projection enters The open-ended groove in the carrier it is not desirable to prevent rotation of the plunger rod. Accordingly, cutouts 71 are provided in the plunger rod to allow rotation of the plunger rod with respect to the barrel when the radially directed projection 55 is in open-ended groove 57. Rotation is allowed because the cutouts 71 are deeper than the projection distance of tab 70. As will be described in more detail hereinafter, tabs 70 also serve as a locking means to hold the plunger rod in the retracted position after the needle is withdrawn into the barrel.

After medication is expelled and the plunger rod is rotated clockwise to engage the carrier so that the radially directed projection 55 is locked in circumferential portion 59 of open-ended groove 57, the plunger rod is permanently attached to the carrier. To disconnect the carrier from the barrel additional clockwise rotational force is applied to the plunger rod flange 50, as best illustrated in FIG. 9. This additional rotation causes needle carrier 28 to rotate clockwise disengaging inwardly directed projections 65 from the closed proximal ends 62 of control groove 61 by forcing the projection past the area of reduced depth 67 in each control groove and forcing the projection 65 into the open distal ends 61 of the control grooves. At this point, the user may then pull the plunger rod in a proximal direction with respect to the barrel, to draw the carrier and the needle into the barrel past the open distal end, as illustrated in FIG. 10. At this point, the syringe assembly may be safely delivered to a disposal container.

Another feature of the present invention is that the plunger rod contains an area of reduced thickness 53. The plunger rod may be withdrawn from the barrel to a position where the area of reduced thickness is outside of the barrel. At this point the plunger rod may be subjected to a bending force which will cause the proximal portion of the plunger rod to break from the distal portion of the plunger rod as illustrated in FIG. 11. This feature further renders the syringe assembly unusable and helps prevent accidental movement of the needle carrier in a distal direction to re-expose the sharp needle point.

Another safety feature of the present invention is means for locking the plunger rod in the barrel after the needle cannula is retracted into the barrel. In the preferred embodiment, locking is accomplished through interaction of locking flange 54 on the plunger rod and inwardly projecting tabs 70 in the barrel. Upon withdrawing the needle carrier into the barrel, the user continues to pull the needle carrier in a proximal direction until locking flange 54 deflects tabs 70 and becomes trapped therebetween as best illustrated in FIG. 11. At this point, the plunger rod cannot move axially with respect to the barrel. In the preferred embodiment, the tabs which prevent rotation of the plunger rod are also the tabs which trap the locking flange. This does not have to be the case and separate structures can be provided for each means. Additional elements, such as sheet metal structures may be attached to the barrel and/or the plunger to engage each other and lock the plunger rod with respect to the barrel. In embodiments containing the structure for locking the plunger rod with respect to the barrel, the plunger rod should be broken off after the locking mechanism is engaged so that the plunger rod will not come out of the barrel during attempts to break the plunger rod at the area of reduced thickness.

It is also within the purview of the present invention to include a threaded engagement between the barrel and the carrier. For example, the carrier may include a distal threaded projection which mates with a threaded portion in the barrel. The threads only function to connect the syringe barrel and the carrier and the function of the syringe with respect to moving the needle assembly and carrier into the barrel is exactly as described above except it is accomplished with more rotational motion of the plunger rod. With a threaded connection the threads should be in a direction to allow the user to rotate the carrier in the proper direction for unlocking. A wide variety of structures are capable of allowing the engagement of the carrier with the barrel, and those structures described hereinabove are representative of these many possibilities, which are within the purview of the present invention.

Figure 12:
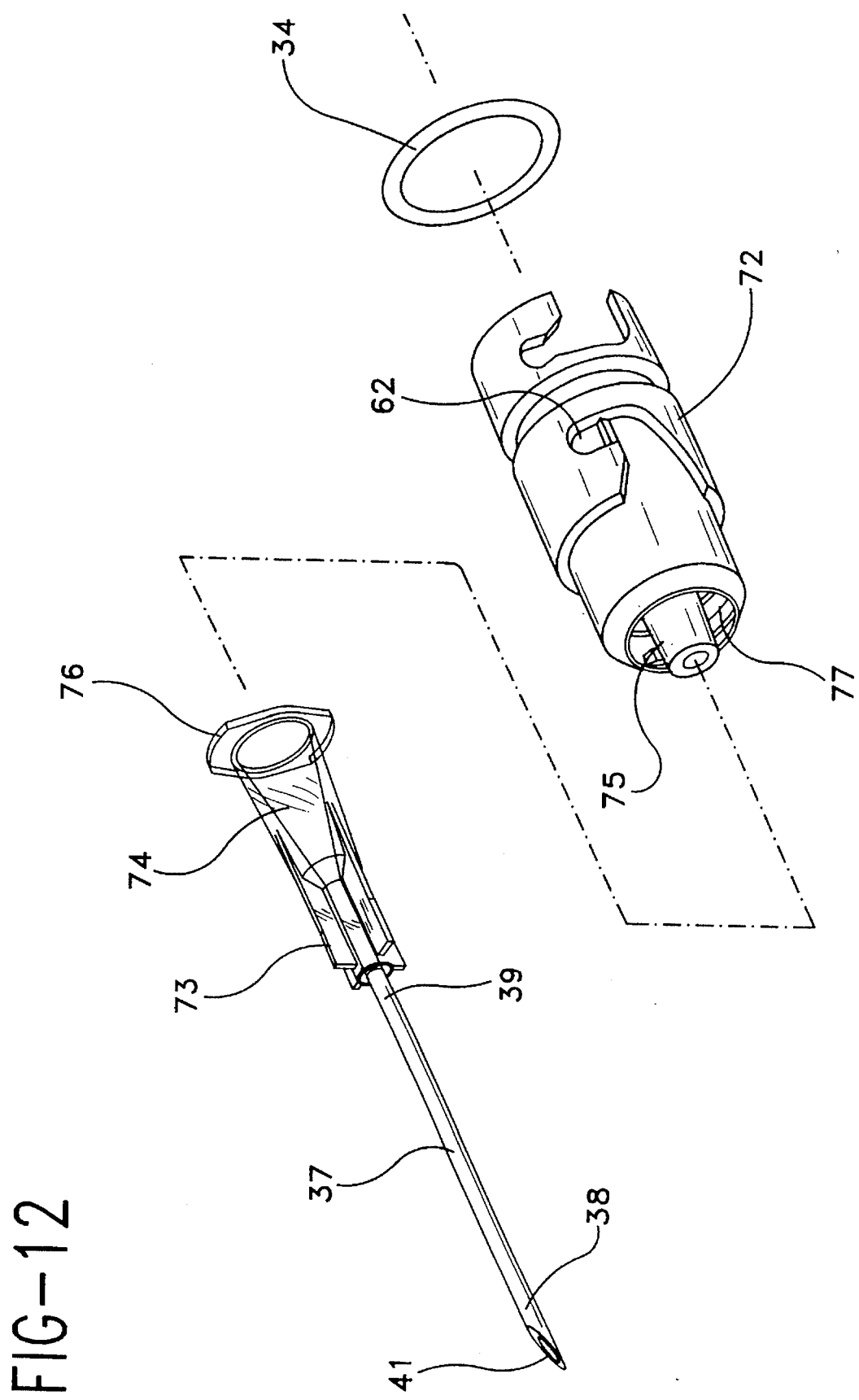
FIG. 12 is an alternative embodiment of the carder and needle of the present invention.

FIG. 12 illustrates an alternative needle carrier of the present invention. In this embodiment, the needle cannula is pan of a needle assembly 73 which includes needle cannula 37 and hub 74. The needle hub and the needle carrier 72 contain cooperating structure so that the needle assembly is removably attached to the carrier. The needle hub includes a frusto-conically shaped interior structure adapted to frictionally engage a tapered luer tip 75 at the distal end of the carrier. To further facilitate engagement of the needle hub to the carrier, projections 76 on the proximal end of the hub engage an internal helical groove 77 of the carrier so that rotation of the needle with respect to the carrier causes the projections to be drawn proximally along the helical groove to tighten and secure the frictional engagement of the tapered luer tip 75 with the frusto-conically shaped recess of hub 74. The needle assembly described herein is a known and commercially available needle assembly, designed to cooperate with syringes or other fittings having male locking luer-type fittings. In all other respects, the alternative carrier illustrated in FIG. 12 functions in the same manner and cooperates with the same plunger and syringe barrel as illustrated in the embodiment of FIGS. 1–11.

FIG. 13 illustrates an alternative needle carrier and plunger of the present invention. In this embodiment needle carrier 78 includes open ended groove 107 having an axial portion 108 and a circumferential portion 109. Plunger 92 includes distal end 94 having radially directed projection 105. In this embodiment, the radially directed projection is circularly shaped.

In some applications, such as when the syringe is used to obtain a human blood sample, it may be desirable, after the syringe has been used, to withdraw any fluid remaining in the lumen of the needle cannula back toward the chamber of the barrel, so that the fluid may not be accidentally discharged into the environment. This function can be accomplished by a slight proximal motion of the plunger with respect to the barrel to draw the fluid toward the chamber. The embodiment of FIG. 13 is designed to provide such proximal motion of the plunger with respect to the barrel. Specifically, circumferential portion 109 of open ended groove 107 is directed proximally so that as radially directed projection 105 on plunger 92 enters circumferential potion 109, said plunger is forced to move in a proximal direction with respect to the barrel as radial directed projection moves along the circumferential portion which is proximally directed. The slight proximal motion of the plunger with respect to the barrel causes fluid in the needle cannula to be drawn toward or into the syringe barrel. In this embodiment, the radially directed projection 105 is circularly shaped. In all other respects, the plunger and the carrier of the embodiment of FIG. 13 function in substantially the same way as the plunger and the carrier of the embodiment of FIGS. 1–11.

The barrel of the safety needle syringe of the present invention may be constructed of a wide variety of materials with thermoplastic and glass materials being preferred. Inwardly facing projections at the distal end of the barrel may be formed of the barrel material or be formed of additional components made of suitable rigid materials such as thermoplastic and corrosion resistant metal such as stainless steel.

The plunger rod and the carrier of the present invention can be made through a wide variety of materials with thermoplastic materials such as polypropylene, polyethylene and polystyrene being desirable. A wide variety of material such as natural rubber, synthetic rubber and thermoplastic elastomers are suitable for forming the annular elastomeric ring and the annular sealing ring. For embodiments of the present invention which are desirably sterile, the materials used for the components should be chosen to withstand the sterilization process utilized.

Thus, it can be seen that the present invention provides a simple, straight-forward, reliable, easily fabricated retractable needle syringe having locking structure for holding the needle in a position with respect to the barrel which is strong enough to resist the often substantial forces experienced during normal use and which is easily de-activated to lower the force required for withdrawing the needle into the barrel. The present invention provides a retractable needle syringe that does not waste medication by requiring additional axial motion of the plunger rod to secure the plunger rod to the needle carrier. The present invention also provides a one-way locking mechanism so that when the plunger rod is secured to the carrier it will not disconnect from the carrier; finally, when the needle is withdrawn inside the barrel there is a need for the locking mechanism to prevent the needle from being later moved so that it projects out of the barrel.

What is claimed is:

1. A retractable needle syringe comprising:

an elongate barrel having an inside surface defining a chamber, an open proximal end and a distal end;

an elongate plunger slidably positioned in fluid-tight engagement with said inside surface of said barrel, said plunger having a distal end, a proximal end extending outwardly from said open end of said barrel, and a radially directed projection on said distal end of said plunger;

a movable needle carrier positioned in fluid-tight engagement with said inside surface of said barrel at said distal end of said barrel, said carrier having an outside surface, a distal end, a proximal end, and a passageway therethrough in fluid communication with said chamber;

said proximal end of said carrier including an open-ended groove, said groove sized and shaped to receive said plunger projection, said groove having an axial portion and a circumferential portion; said plunger being movable axially, distally and proximally, so that said plunger projection can enter and exit said axial portion of said groove, rotation of said plunger with respect to said carrier causes said projection to containing said projection so that said plunger can apply axially directed force and rotationally directed force to said carrier;

a needle cannula projecting outwardly from said distal end of said carrier, said cannula having a distal end, a proximal end and lumen therethrough in fluid communication with said passageway;

control means for helping to prevent movement of said carrier with respect to said barrel during normal use of said syringe while said control means is in a first locked position, and for allowing said carrier to be moved proximally into said chamber through forces applied to said plunger while said control means is in a second unlocked position, transition between said first locked position and said second unlocked position and withdrawing said cannula into said barrel bring accomplished by at least two motions of said plunger with respect to said barrel while said distal end of said plunger engages said carrier, said first motion being rotational to rotate said carrier with respect to said barrel through an acute angular rotation followed by a second axial motion proximally directed to move said carrier into said barrel far enough so that said distal end of said cannula does not extend beyond said distal end of said barrel.

2. The syringe of claim 1 further including means for aligning said plunger with respect to said barrel so that said radially directed projection on said plunger enters said open-ended groove upon distally directed axial motion of said plunger without rotation of said plunger with respect to said carrier.

3. The syringe of claim 1 wherein said plunger includes a longitudinal groove and said barrel includes an inwardly directed tab positioned within said longitudinal groove in said plunger to align said radially directed projection on said plunger with said axial portion of said open-ended groove on said proximal end of said carrier so that said projection enters said open-ended groove upon distal motion of said plunger without rotation of said plunger with respect to said carrier.

4. The syringe of claim 1 further including means for locking said radially directed projection on said plunger rod in said circumferential portion of said open-ended groove.

5. The syringe of claim 1 wherein said radially directed projection on said plunger and said circumferential portion of said open-ended groove are configured so that when said projection is positioned in said circumferential portion said projection is locked in said circumferential portion.

6. The syringe of claim 5 wherein said circumferential portion of said groove includes an area of reduced width being shaped to allow said projection to be forcibly passed therethrough in one direction only.

7. The syringe of claim 1 wherein said radial directed projection has a circular shaped cross-section.

8. The syringe of claim 1 wherein said distal end of needle cannula includes a sharp edge.

9. The syringe of claim 1 wherein said needle is removably attached to said carrier.

10. The syringe of claim 1 wherein said needle cannula includes a proximal end connected to a hub, said hub being removably connected to said carrier.

11. The syringe of claim 1 wherein said carrier includes an annular elastomeric ring extending around the periphery of said carrier, between said carrier and said barrel, for forming a fluid-tight seal between said outside surface of said carrier and said inside surface of said barrel.

12. The syringe of claim 1 wherein said control means includes a control groove in said carrier, said control groove including a closed proximal end and an open distal end, and a projection on said inside surface of said barrel positioned within said control groove when said carrier is at said distal end of said barrel, said projection preventing proximal and distal motion of said carrier with respect to said barrel when said projection is in said closed end and allowing proximal motion of said carrier when said projection is in said open end.

13. The syringe of claim 12, wherein said control groove includes an area of reduced width adjacent to said closed end, said area of reduced width being smaller than the distance across said projection so that additional rotational force is required to move said carrier into and out of a position where said projection is positioned at said closed end of said control groove.

14. The syringe of claim 12 wherein said control groove includes an area of reduced depth adjacent to said closed end, said area of reduced depth being configured so that additional rotational force is required to move said carrier into and out of a position where said projection is positioned at said closed end of said groove.

15. The syringe of claim 12 wherein said projection has a circularly shaped cross-section.

16. The syringe of claim 12 further including a second control groove in said carrier opposed from said control groove and a second projection on said barrel opposed from said projection, said second projection being positioned in said second control groove when said carrier is at said distal end of said barrel.

17. The syringe of claim 1 wherein said plunger includes a frangible zone between said distal end of said plunger and said proximal end of said plunger so that the proximal end of the plunger can be disconnected from the distal end of the plunger means after said carrier is moved into said barrel far enough so that said distal end of said cannula does not extend beyond said distal end of said barrel.

18. The syringe of claim 1 further including means for locking said plunger in said barrel after said needle cannula is retracted into said barrel.

19. The syringe of claim 18 wherein said means for locking said plunger includes an outwardly directed protuberance on said plunger and two inwardly directed tabs on said barrel, said tabs being shaped to deflect to accept and trap said protuberance when said plunger rod is moved proximally with respect to said barrel.

20. The syringe of claim 1 further including means for withdrawing fluid from said needle cannula as said plunger is rotated with respect to said carrier causing said radially directed projection to enter said circumferential portion of said open-ended groove.

21. The syringe of claim 20 wherein said means for withdrawing fluid from said needle cannula includes said circumferential portion of said open-ended groove being proximally directed so that as said radially directed projection on said plunger enters said circumferential portion, said plunger is forced to move in a proximal direction with respect to said barrel through interaction of said projection and said circumferential portion of said groove.

* * * * *